United States Patent
Shigemori

(10) Patent No.: US 8,348,832 B2
(45) Date of Patent: Jan. 8, 2013

(54) INTRA-SUBJECT INFORMATION ACQUIRING SYSTEM

(75) Inventor: Toshiaki Shigemori, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1097 days.

(21) Appl. No.: 11/658,826

(22) PCT Filed: Apr. 6, 2006

(86) PCT No.: PCT/JP2006/307339
§ 371 (c)(1),
(2), (4) Date: Nov. 7, 2008

(87) PCT Pub. No.: WO2006/109676
PCT Pub. Date: Oct. 19, 2006

(65) Prior Publication Data
US 2009/0076320 A1    Mar. 19, 2009

(30) Foreign Application Priority Data
Apr. 7, 2005 (JP) .................................. 2005-111131

(51) Int. Cl.
*A61B 1/04* (2006.01)
*A61B 1/06* (2006.01)
(52) U.S. Cl. .................... 600/118; 600/112; 600/160
(58) Field of Classification Search .................. 600/103, 600/109, 112, 117, 118
See application file for complete search history.

(56) References Cited

U.S. PATENT DOCUMENTS

| 6,275,255 | B1 | 8/2001 | Adair et al. | |
|---|---|---|---|---|
| 2001/0002842 | A1 | 6/2001 | Ozawa | |
| 2003/0073935 | A1* | 4/2003 | Segawa et al. | 600/593 |
| 2003/0085994 | A1 | 5/2003 | Fujita et al. | |
| 2003/0195396 | A1 | 10/2003 | Scarantino et al. | |
| 2004/0225189 | A1* | 11/2004 | Kimoto et al. | 600/160 |
| 2004/0249291 | A1 | 12/2004 | Honda et al. | |
| 2005/0038321 | A1 | 2/2005 | Fujita et al. | |

FOREIGN PATENT DOCUMENTS

| JP | 2003-19111 | 1/2003 |
|---|---|---|
| JP | 2004-167163 | 6/2004 |
| JP | 2005-021516 | 1/2005 |

OTHER PUBLICATIONS

Extended European Search Report dated Oct. 14, 2010.

* cited by examiner

*Primary Examiner* — Clayton E Laballe
*Assistant Examiner* — Leon W Rhodes, Jr.
(74) *Attorney, Agent, or Firm* — Scully, Scott, Murphy & Presser, P.C.

(57) ABSTRACT

A viewer 4 as a compact display device displays a body cavity image picked up by a capsule endoscope 3. When a communication-cable connection detector 48 detects a communication cable connection between a receiving apparatus 2 and the viewer 4, a control unit 49 switch controls a changeover switch 44 based on this connection detection, thereby switching a display of an LCD 41 to a display of image data from wire. Next, information necessary for an examination such as image data is taken in from the receiving apparatus 2 via a communication cable 5, and is displayed in an LCD 41. With this arrangement, a display unit is not necessary in the receiving apparatus 2, and a circuit configuration becomes simple. The receiving apparatus can be made compact and light, and power consumption can be decreased.

36 Claims, 6 Drawing Sheets

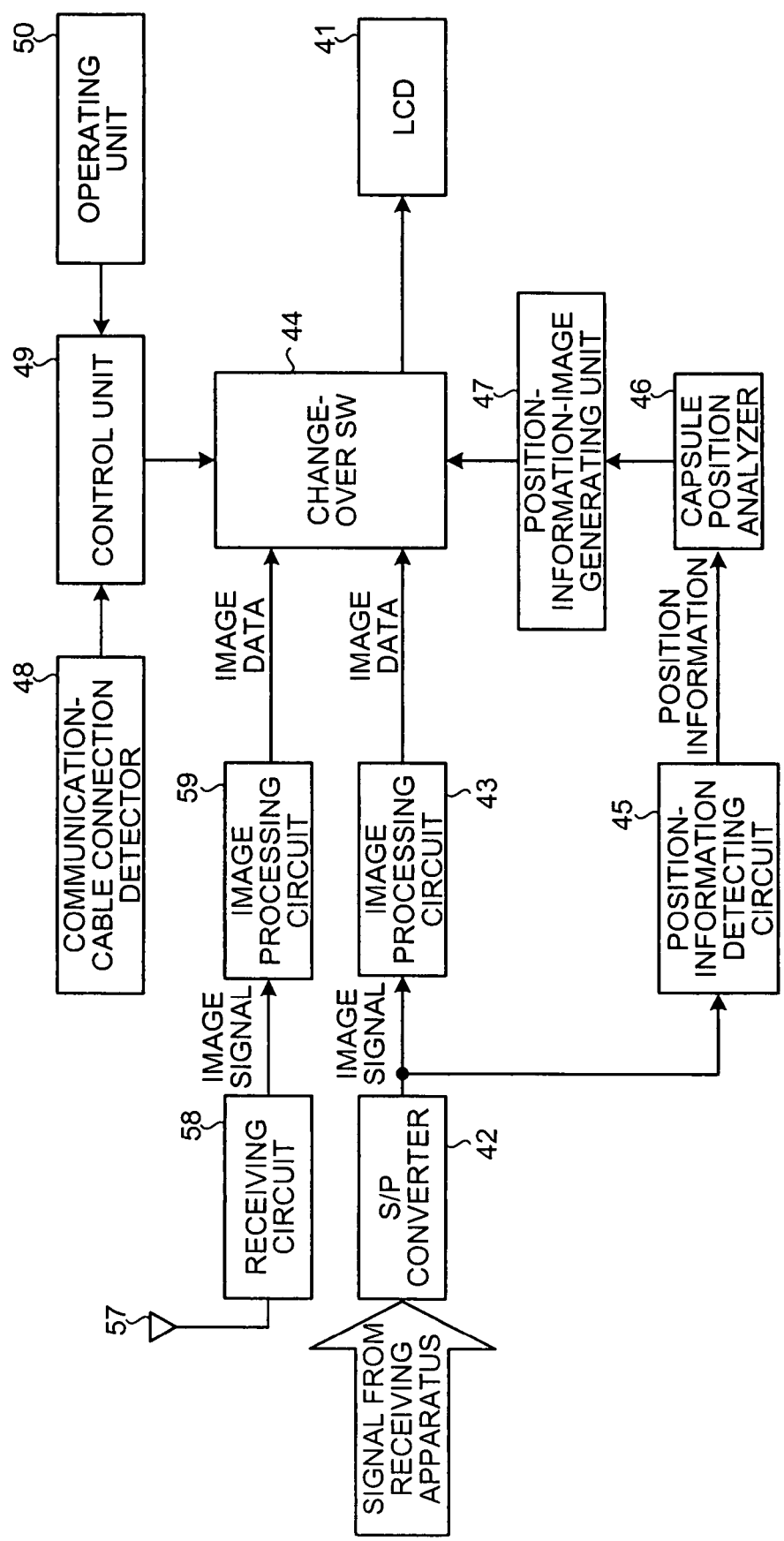

INTRA-SUBJECT INFORMATION ACQUIRING SYSTEM

TECHNICAL FIELD

The present invention relates to an intra-subject information acquiring system that receives and displays an image signal that is radio transmitted from a body-insertable apparatus, such as a swallowable capsule endoscope, inserted into a subject.

BACKGROUND ART

In recent years, a capsule endoscope having an imaging function and a radio communication function has appeared in the field of endoscope. The capsule endoscope is swallowed by a subject from the mouth for an observation (examination), moves within internal organs (within body cavities) such as a stomach and a small intestine, along peristaltic motions thereof, and sequentially images using the imaging function, until naturally discharged from the body (human body).

During the observation period while the capsule endoscope is moving within the internal organs, image data acquired within the body cavity by the capsule endoscope is sequentially transmitted to the outside of the subject by the radio communication function such as radio communication, and is stored in a memory provided within a receiving apparatus outside. When the subject carries the receiving apparatus having the radio communication function and the memory function, the subject can move freely even during the observation period after swallowing the capsule endoscope until the capsule endoscope is discharged. After the observation, a doctor or a nurse can perform diagnosis by displaying the images of the body cavity onto a display unit such as a display, based on the image data stored in the memory of the receiving apparatus.

In general, a receiving apparatus has plural antennas disposed dispersedly at the outside of the subject to receive image signals transmitted from the capsule endoscope, and selectively switches one antenna having a small error in the reception of the image signal to receive the image signal. Patent Document 1 describes a receiver that switches between plural antennas disposed at the outside of a subject for reception, and locates a position of a capsule endoscope within the subject as a transmission source of the image signal, based on electric-field strength that each antenna receives.

Patent Document 1: Japanese Patent Application Laid-open No. 2003-19111

DISCLOSURE OF INVENTION

Problem to be Solved by the Invention

Some of the receiving apparatuses, however, include a small display device to display a received image signal and position information of a capsule endoscope, and the receiving apparatus itself can be large and heavy. When a subject carries such receiving apparatus, the subject has to bear a large load. Further, the receiving apparatus consumes large power to carry out control of display on the display device, image processing, and calculation of position information. On the other hand, some receiving apparatuses are connected to a workstation having a display, and transmits an acquired image signal, position information of a capsule endoscope, or the like to the workstation, so that the information is displayed on the display device. In such case, the receiving apparatus cannot promptly display the information received from the capsule endoscope. When the receiving apparatus is connected to the workstation while the subject carries the receiving apparatus, an antenna attached to the subject becomes connected to ground, whereby insulation is necessary.

The present invention has been achieved in view of the above. It is an object of the present invention to provide an intra-subject information acquiring system that can have a small and light receiving apparatus and that can decrease power consumption.

It is another object of the present invention to provide an intra-subject information acquiring system that can promptly display necessary information such as intra-subject information acquired from a capsule endoscope in real time.

Means for Solving Problem

An intra-subject information acquiring system according to one aspect of the present invention includes a receiving apparatus that receives intra-subject information radio transmitted from a body-insertable apparatus inserted into a subject, a compact display device that takes in and displays the intra-subject information on a display unit, and a communication unit that connects between the receiving apparatus and the compact display device in a communicable manner, wherein the receiving apparatus outputs at least the intra-subject information to the compact display device via the communication unit, and the compact display device includes a detector that detects a connection between the compact display device and the receiving apparatus by the communication unit, and a switching controller that switches a display of the display unit to a display of the intra-subject information taken in via the communication unit, based on a result of detection by the detector.

An intra-subject information acquiring system according to another aspect of the present invention includes a receiving apparatus that receives intra-subject information radio transmitted from a body-insertable apparatus inserted into a subject, a compact display device that takes in and displays the intra-subject information on a display unit, and a communication unit that connects the receiving apparatus and the compact display device in a communicable manner, wherein the receiving apparatus outputs at least the intra-subject information to the compact display device via the communication unit, and the compact display device includes a detector that detects a connection between the compact display device and the receiving apparatus by the communication unit, a radio unit that receives intra-subject information radio transmitted from the body-insertable apparatus, and a switching controller that switch controls a reception operation performed by the radio unit or the communication unit, based on a result of detection by the detector.

According to an intra-subject information acquiring system, the intra-subject information that the body-insertable apparatus transmits may include at least an image signal acquired by imaging of an interior of the subject, the receiving apparatus may further include a receiving antenna that receives intra-subject information from the body-insertable apparatus, a received strength detector that detects received strength in the receiving antenna, and a superimposing unit that superimposes information of received strength detected by the received strength detector, onto the intra-subject information, and the compact display apparatus may further include an analyzer that analyzes a position of the body-insertable apparatus, based on information of the received strength, and an instructing unit that instructs information displayed on the display unit, and the switching controller may switch information displayed on the display unit, according to an instruction of the instructing unit.

In the intra-subject information acquiring system, the intra-subject information that the body-insertable apparatus transmits may include at least an image signal acquired by imaging an interior of the subject, and position information of the body-insertable apparatus, the compact display device may further include an instructing unit that instructs information to be displayed on the display unit, and the switching controller may switch information displayed on the display unit, according to an instruction of the instructing unit.

In the intra-subject information acquiring system, the information displayed on the display unit may include the image signal, information concerning the body-insertable apparatus, information concerning the receiving apparatus, the position information of the body-insertable apparatus, information concerning an examination of the subject, and identification information of the subject, and the display unit may display at least one piece of information among these pieces of information, according to a display switching by the switching controller.

In the intra-subject information acquiring system, the identification information of the subject may include at least one of a patient ID identifying the subject, a patient name, and an age.

In the intra-subject information acquiring system, the information concerning the examination of the subject may include at least one of an examination ID of the subject and a time of examination.

In the intra-subject information acquiring system, the information concerning the body-insertable apparatus may include at least one of a capsule ID identifying the body-insertable apparatus, and a remaining battery charge of the body-insertable apparatus.

In the intra-subject information acquiring system, the information concerning the receiving apparatus may include at least one of a receiving apparatus ID identifying the receiving apparatus, a remaining battery charge of the receiving apparatus, a receiving state of a radio signal from the body-insertable apparatus, and an alarm issued by the receiving apparatus.

In the intra-subject information acquiring system, the communication unit may be a communication cable including a USB cable or a 232C cable, and the receiving apparatus may transmit information to be displayed on the display unit via the communication cable to the compact display device.

In the intra-subject information acquiring system, the receiving apparatus may superimpose information to be displayed on the display unit onto the image signal, and may transmit a resulting superimposed image signal to the compact display device via the communication unit.

In the intra-subject information acquiring system, the compact display device may further include a changeover switch to selectively switch the information displayed on the display unit among the image signal, the information concerning the body-insertable apparatus, the information concerning the receiving apparatus, the position information of the body-insertable apparatus, the information concerning the examination of the subject, and the identification information of the subject, and the switching controller may switch control the changeover switch.

Effect of the Invention

In the intra-subject information acquiring system according to the present invention, a receiving apparatus and a compact display device are connected via a communication unit. When a detector detects that the communication unit connects the receiving apparatus and the compact display device, the switching controller performs display switching so as to enable the display unit to take in the intra-subject information from the receiving apparatus and to display the intra-subject information. Therefore, the receiving apparatus is not required to be provided with a display unit, and a circuit configuration is simplified, whereby the receiving apparatus can be made compact and light, and power consumption can be decreased. Further, in the intra-subject information acquiring system according to the present invention, the compact display apparatus connected to the receiving apparatus takes in information such as intra-subject information necessary for the examination, and displays the taken-in information on the display unit. Therefore, necessary information such as intra-subject information acquired from a capsule endoscope can be promptly displayed in real time on the display unit.

BRIEF DESCRIPTION OF DRAWINGS

FIG. 7 is a block diagram showing a configuration of a viewer, which is a compact display device like that shown in FIG. 1, according to a second embodiment.

EXPLANATIONS OF LETTERS OR NUMERALS

Figure 1:
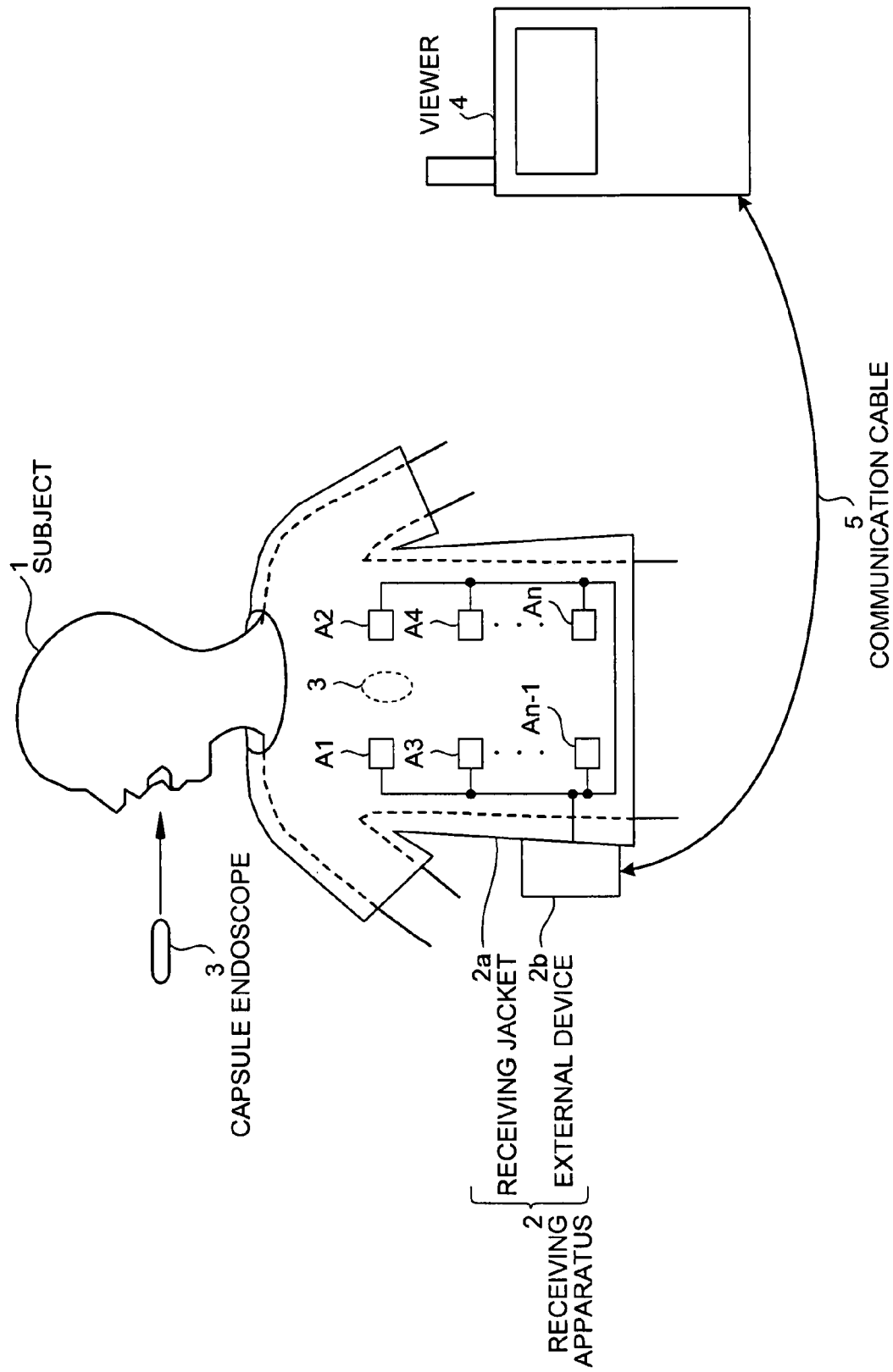
FIG. 1 is a schematic diagram showing an overall configuration of an intra-subject information acquiring system according to the present invention.

1 Subject
2 Receiving apparatus
2a Receiving jacket
2b External device
3 Capsule endoscope
4 Viewer
5 Communication cable
11 Tuner
12 Binarizing circuit
13 Superimposing unit
14 Interface unit
15 Sample-and-hold circuit
16 A/D converter
Power supply unit
18, 56 Power switch
21 Connector
22 Projection
41 Display unit
42 S/P converter
43, 59 Image processing circuit
44 Changeover switch
45 Position-information detecting circuit 45
46 Capsule position analyzer
47 Image generating unit
48 Communication-cable connection detector
49 Control unit 50 Operating unit
51, CON Connecting unit
52 Contact pin
53 Spring
54, 55 Electric path
57, A1 to An Receiving antenna
58 Receiving circuit
CON1 to CONn Connector

BEST MODE(S) FOR CARRYING OUT THE INVENTION

Exemplary embodiments of an intra-subject information acquiring system according to the present invention will be explained below in detail with reference to FIGS. 1 to 7. Note that the present invention is not limited to the embodiments, and various modifications of the embodiments can be made without departing from the scope of the present invention.

First Embodiment

FIG. 1 is a schematic diagram showing an overall configuration of an intra-subject information acquiring system according to the present invention. In FIG. 1, a radio intra-subject information acquiring system includes a receiving apparatus 2 having a radio receiving function, and a capsule endoscope (a body-insertable apparatus) 3 that is inserted into a subject 1, picks up images within the body cavity, and transmits data such as an image signal to the receiving apparatus 2. The radio intra-subject information acquiring system also includes a viewer 4 as a compact display device that displays a body-cavity image based on an image signal received by the receiving apparatus 2, and a communication cable 5 as a communication unit that delivers data between the receiving apparatus 2 and the viewer 4 as a compact display device. The receiving apparatus 2 includes a receiving jacket 2a that the subject 1 wears, and an external device 2b that performs processing of a received radio signal.

Figure 2:
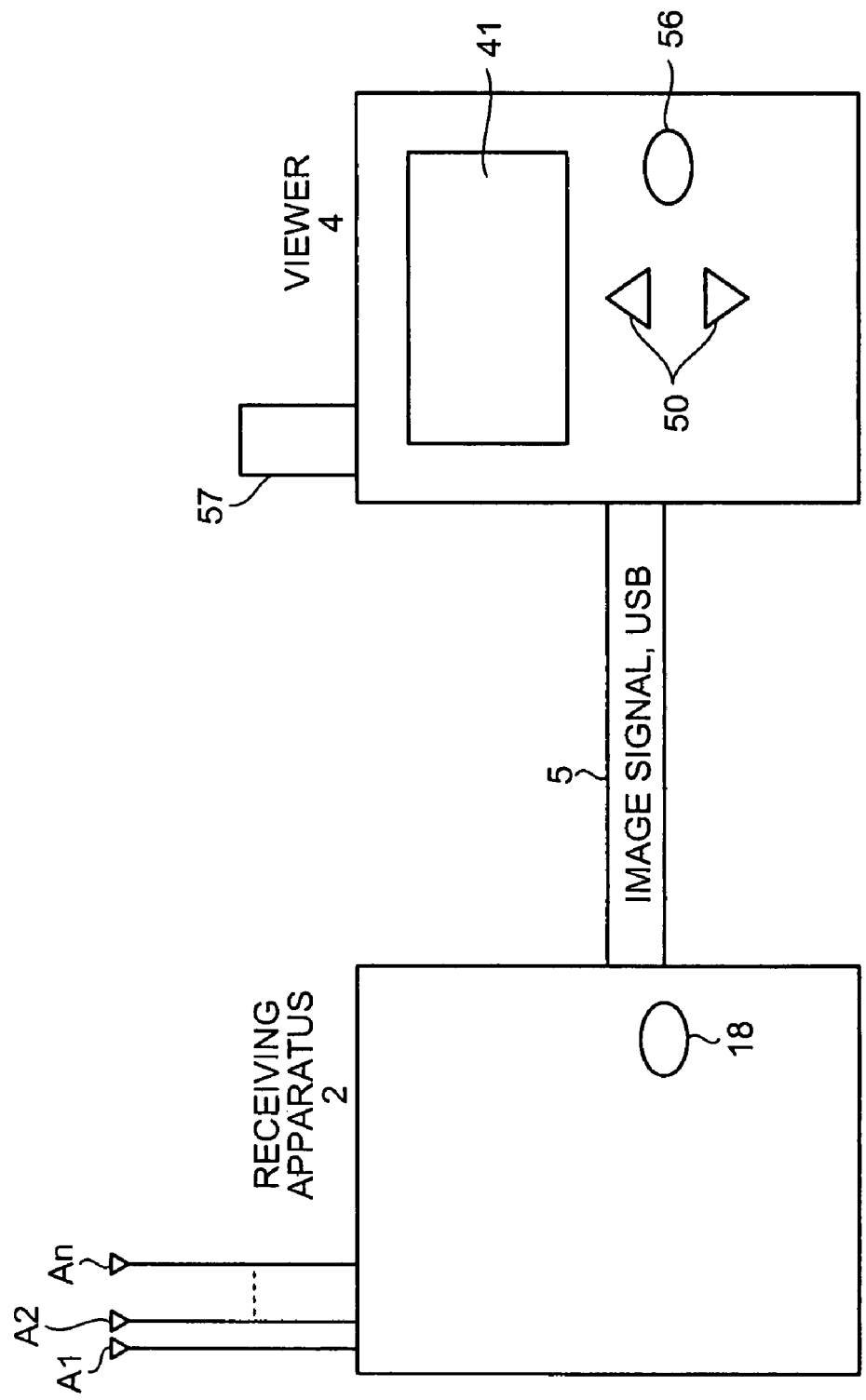
FIG. 2 is a schematic view of a receiving apparatus and a viewer, which is a compact display device, shown in FIG. 1.
Figure 3:
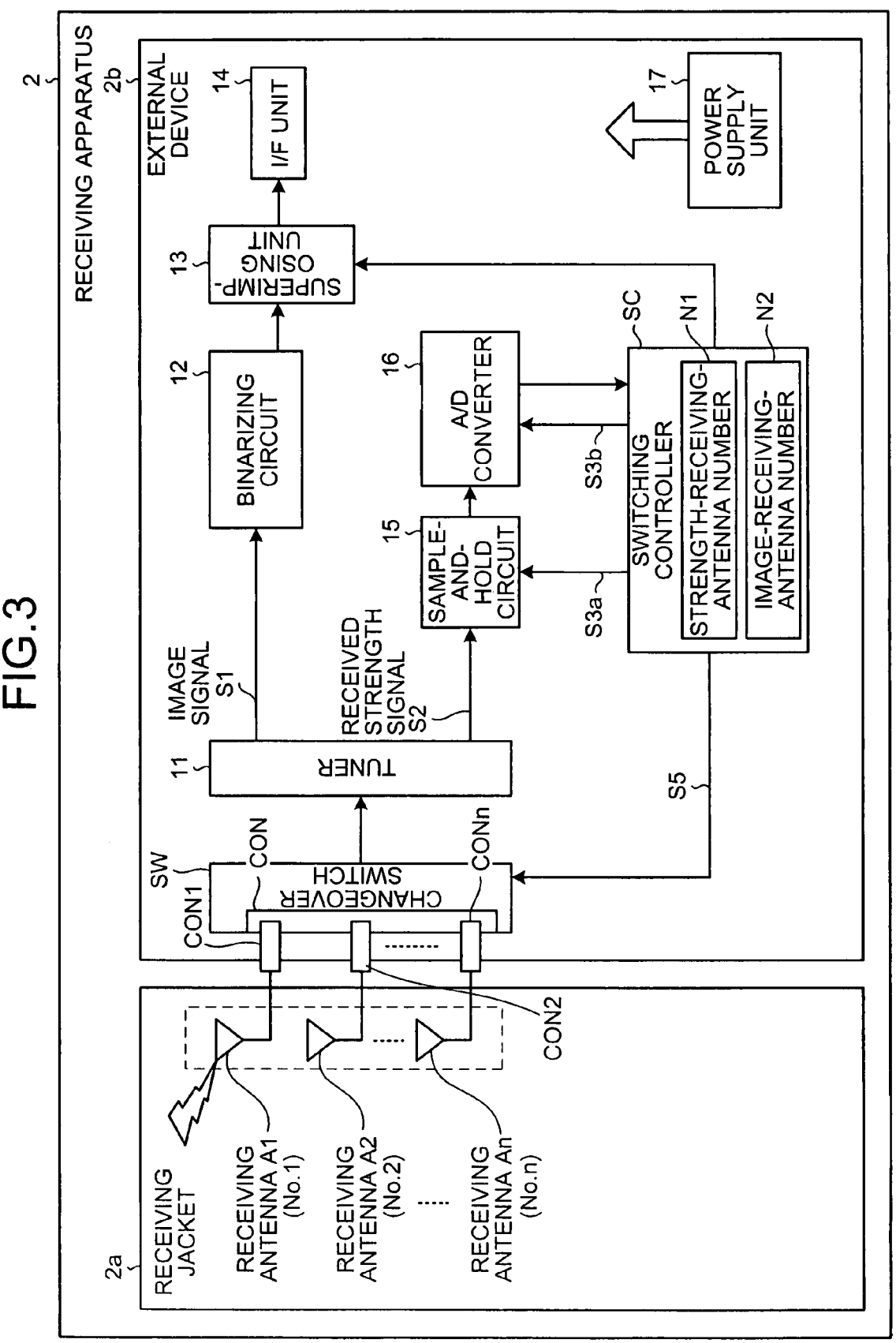
FIG. 3 is a block diagram showing a configuration of the receiving apparatus.

A configuration of the receiving apparatus is explained next with reference to a schematic diagram shown in FIG. 2 and a block diagram shown in FIG. 3. The receiving apparatus 2 has a function of receiving body-cavity image data radio-transmitted from the capsule endoscope 3. As shown in FIGS. 2 and 3, the receiving apparatus 2 has a shape wearable by the subject 1, and includes the receiving jacket 2a having receiving antennas A1 to An, and the external device 2b that processes a radio signal received via the receiving jacket 2a. Each of the receiving antennas A1 to An can be directly adhered to the external surface of the subject (human body) 1 in such a manner that the receiving antennas A1 to An are not attached to the receiving jacket 2a, or can be made detachable from the receiving jacket 2a.

The external device 2b transmits a received image signal to the viewer 4 as a compact display device via the connected communication cable 5. A connector CON is provided on an upper surface of an external surface for the connection to the receiving antennas A1 to An. The receiving antennas A1 to An have connectors CON1 to CONn that connect the receiving antennas to the connector CON. The external device 2b has a function of binarizing a radio signal transmitted from the capsule endoscope 3 and outputting the resulting signal. In other words, as shown in FIG. 3, the external device 2b includes a changeover switch SW that switches a connection of each of the receiving antennas A1 to An, and a tuner 11 that is connected to a latter stage of the changeover switch SW, amplifies a radio signal from the receiving antennas A1 to An of which connection is switched by the changeover switch SW, and demodulates the amplified radio signal. Each of a binarizing circuit 12 and a sample-and-hold circuit 15 are connected to the latter stage of the tuner 11. An A/D converter 16 is connected to a latter stage of the sample-and-hold circuit 15.

The superimposing unit 13 has a function of superimposing information from a switching controller SC onto an image signal binarized by the binarizing circuit 12, as a superimposer, and outputting the result to a interface unit 14 connected thereto. The switching controller SC has a strength-receiving-antenna number N1, and an image-receiving-antenna number N2, instructs a switching of the changeover switch SW, and instructs a processing timing of the sample-and-hold circuit 15 and the A/D converter 16. The interface unit 14 is connected to the communication cable 5 via a connector (not shown). The superimposing unit 13 has an internal memory (not shown), and registers identification information that identifies a subject such as an examination ID input from the outside, into the internal memory. The superimposing unit 13 superimposes information from the switching controller SC onto the image signal, and outputs the superimposed image signal to the interface unit 14. A power supply unit 17 includes a battery embedded in the external device 2b. When a power switch 18 shown in FIG. 2 is turned on, the power supply unit 17 supplies power to each of the above internal devices.

The changeover switch SW of the external device 2b outputs radio signals from the receiving antennas A1 to An to the tuner 11, based on a switch instruction from the switching controller SC. The changeover switch SW has the connector CON as an antenna switch unit that connects each of the receiving antennas A1 to An corresponding to each disposition position of the receiving antennas A1 to An.

In FIG. 3, as described above, the tuner 11 amplifies a radio signal, outputs a demodulated image signal S1 to the binarizing circuit 12, and outputs a received strength signal S2 as received electric-filed strength of the amplified radio signal, to the sample-and-hold circuit 15. The image signal binarized by the binarizing circuit 12 is output to the superimposing unit 13. The A/D converter 16 converts the received strength signal that is sampled and held by the sample-and-hold circuit 15, into a digital signal, and the switching controller SC takes in the resulting digital signal.

The switching controller SC holds the information of a strength-receiving-antenna number N1 and an image-receiving-antenna number N2. The switching controller SC outputs to the changeover switch SW a signal S5 that instructs the changeover switch SW to selectively connect one of the receiving antennas A1 to An corresponding to the strength-receiving-antenna number N1, during a strength receiving period, and that instructs the changeover switch SW to selectively connect one of the receiving antennas A1 to An corresponding to the image-receiving-antenna number N2, during an image receiving period. At the same time, the switching controller SC outputs a signal S3a that instructs a sample-and-hold timing of the sample-and-hold circuit 15, and a signal S3b that instructs an A/D conversion timing of the A/D converter 16. The switching controller SC also outputs information of one of the receiving antennas A1 to An corresponding to the strength-receiving-antenna number N1 that is taken in during the strength reception period, and information of received strength of each of the receiving antennas A1 to An, to the superimposing unit 13.

The superimposing unit 13 superimposes the information of the receiving antennas A1 to An corresponding to the strength-receiving-antenna number N1 and the information of the received strength of each of the receiving antennas A1 to An onto the image signal from the binarizing circuit 12, and outputs the superimposed information to the interface unit 14. The interface unit 14 transmits the image signal to the viewer 4 as a compact display device via the communication cable 5. The superimposing unit 13 according to the present invention can also superimpose the information from the switching controller SC and the identification information registered in the internal memory onto the image signal, and output the superimposed information to the interface unit 14.

Figure 4:
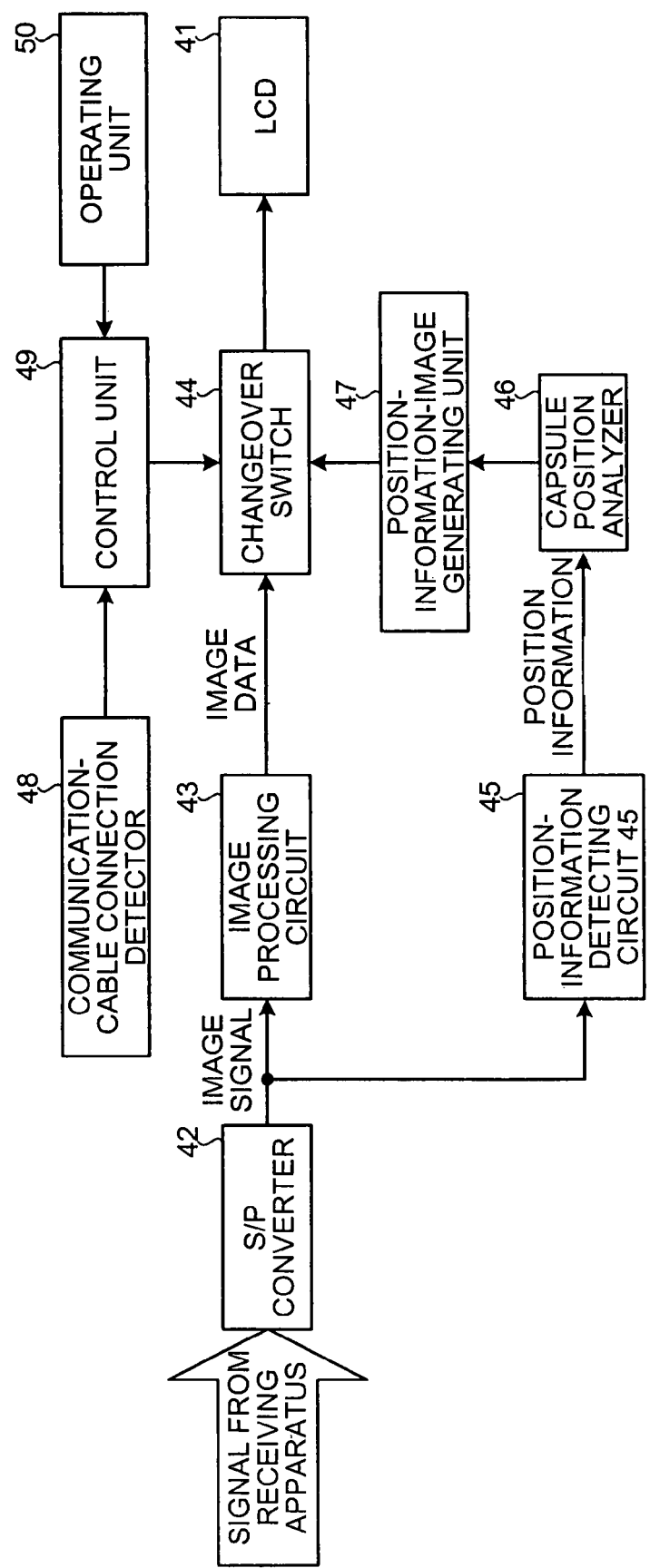
FIG. 4 is a block diagram showing a configuration of a viewer, which is a compact display device, according to a first embodiment.

The viewer 4 as a compact display device displays and analyzes the information taken in from the receiving apparatus 2 via the communication cable 5. In other words, as shown in FIG. 2, the viewer 4 as a compact display device has a liquid crystal display such as an LCD 41 as a display unit, on the external surface. As shown in FIG. 4, the viewer 4 as a compact display device includes a serial/parallel converter 42 that takes in a signal transmitted from the receiving apparatus 2, and performs serial/parallel conversion on the signal. An image signal output from the serial/parallel converter 42 is output to an image processing circuit 43. The image data processed by the image processing circuit 43 is output to the LCD 41 via a changeover switch 44, and displayed by the LCD 41. A power switch 56 is provided on the external surface of the viewer 4 as a compact display device. The communication cable includes a composite cable having a cable that is used to transmit an image signal, and a cable for USB and 232C, and can transmit various kinds of data.

The information of the receiving antennas A1 to An corresponding to the strength-receiving-antenna number N1 and the information of received strength output from the serial/parallel converter 42 are supplied to the position-information detecting circuit 45. The position-information detecting circuit 45 selects a receiving antenna that receives largest received electric-field strength as a receiving antenna, based on the information of the taken-in received strength, and sequentially outputs a number of the selected receiving antenna as position information, to a capsule position analyzer 46.

The capsule position analyzer 46 analyzes the position of the capsule endoscope 3 within the body cavity of the subject, and outputs information on the result of analysis to a position-information-image generating unit 47. The position-information-image generating unit 47 generates and supplies an intra-subject map via the changeover switch 44 to the LCD 41, which displays the intra-subject map together with the position of the capsule endoscope 3 as analyzed by the capsule position analyzer 46.

Figure 5:
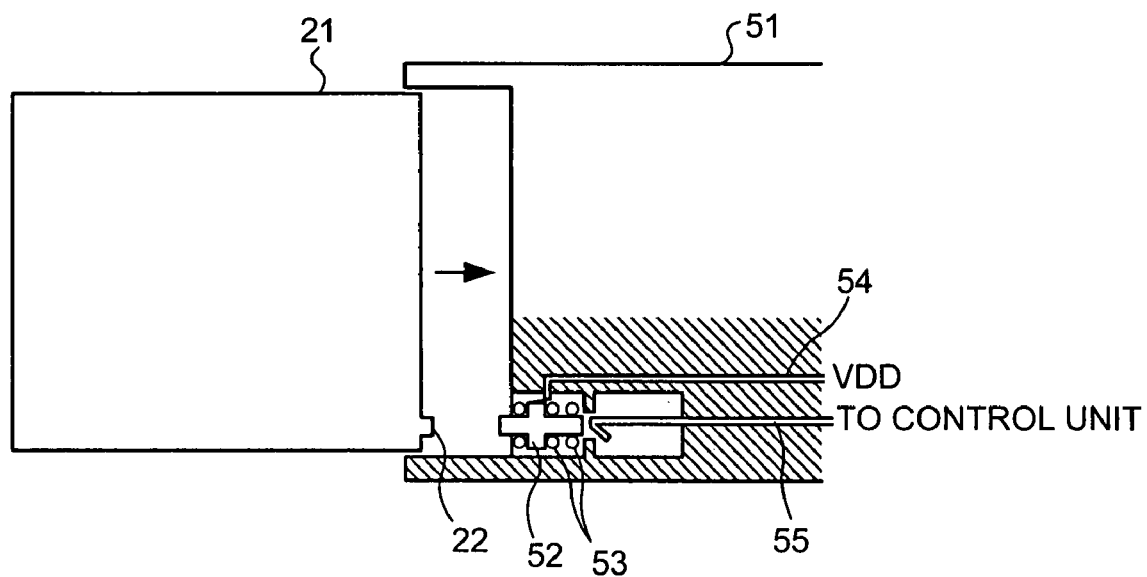
FIG. 5 is a schematic view of showing a configuration of a connecting unit that includes an example of a communication-cable connection detector.

The viewer 4 as a compact display device includes a communication-cable connection detector 48, which detects a connection of the communication cable 5 to the receiving apparatus 2. As shown in FIG. 5, in the communication-cable connection detector 48, a connecting unit 51 of the communication cable 5 includes a contact pin 52 that is electrically connected to a constant voltage source VDD, and a spring 53 that biases the contact pin 52 to push out the contact pin 52 to the outside. A projection 22 is provided in a connector 21 of the receiving apparatus at a predetermined position opposing to the contact pin 52 of the connecting unit 51. When the connector 21 is fitted to the connecting unit 51, the projection 22 is brought into contact with the contact pin 52, thereby pressing the contact pin 52 to the inside of the connecting unit 51. Because of the pressing, the contact pin 52 is brought into contact with both an electric path 54 at the constant voltage source VDD side, and an electric path 55 at the side of a control unit 49, and a detection signal is output to the control unit 49. When the connector 21 is removed from the connecting unit 51, the projection 22 is separated from the contact pin 52, and the contact pin 52 returns to the original position due to the biasing force of the spring 53. Therefore, the contact pin 52 is brought into a non-contact state with the electric path 55 at the control unit 49 side, and the output of a detection signal to the control unit 49 ceases.

The control unit 49 has a function as a switching unit that switches the display of the LCD 41. In other words, when a detection signal is input from the communication-cable connection detector 48, the control unit 49 switch controls the changeover switch 44, and switches the display of the LCD 41 to the display of information taken in via the communication cable 5. An operating unit 50 configured by a display changeover switch and the like of the display unit 41 shown in FIG. 2 is connected to the control unit 49. The control unit 49 switch controls the changeover switch 44, based on a display switch instruction of the operating unit 50, selects the information taken in via the communication cable 5, and displays the selected information on the LCD 41.

In other words, when the communication cable 5 is connected to the receiving apparatus 2, and when a detection signal is input from the communication-cable connection detector 48, the control unit 49 switch controls the changeover switch 44, thereby connecting the image processing circuit 43 with the LCD 41 and displaying the image data on the LCD 41. When a display switch instruction is input from the display changeover switch of the operating unit 50, the control unit 49 switch controls the changeover switch 44, based on the instruction, thereby connecting the position-information-image generating unit 47 with the LCD 41, and displaying the intra-subject map generated by the image generating unit 47 and the position of the capsule endoscope 3 on the intra-subject map, on the LCD 41.

Figure 6:
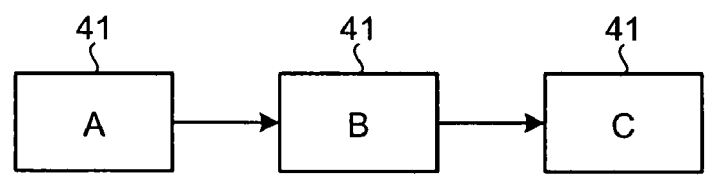
FIG. 6 is a schematic diagram for explaining switching of a display device of a viewer as a compact display device.

The information displayed on the LCD 41 is not limited to the image data and the position information of the capsule endoscope, and can also include identification information of the subject such as the patient ID mentioned above, a patient name, and age of a patient, information concerning an examination such as a time of examination and an examination ID, information concerning the capsule endoscope such as a capsule ID and remaining battery charge of the capsule, and information concerning the receiving apparatus such as a receiving apparatus ID, a remaining battery charge of the power supply unit 17, a radio signal receiving state, and an alarm issued by the receiving apparatus. These pieces of information can be superimposed on the image signal, and can be transmitted from the receiving apparatus 2 to the viewer 4 as a compact display device. Alternatively, these pieces of information can be registered in an internal memory (not shown) inside the viewer 4 as a compact display device, for example, within an internal memory in the control unit 49, and corresponding information can be made displayed at least on one LCD 41, based on a display switch instruction of the operating unit 50 that can specify a piece of information. For example, as shown in FIG. 6, when the screen of the LCD 41 is A, image data can be displayed. When the screen of the LCD 41 is B, information concerning an examination such as an examination ID and a time of examination can be displayed based on a display switch instruction issued by the operating unit 50. When the screen of the LCD 41 is C based on the next display switch instruction of the operating unit 50, the intra-subject map and the position of the capsule endoscope 3 can be displayed.

As described above, in the present embodiment, the viewer 4 as a compact display device displays a body-cavity image picked up by the capsule endoscope 3. Based on a result of detection by the communication-cable connection detector 48, the control unit 49 controls the changeover switch 44, thereby switching the display of the LCD 41. Information necessary for the examination such as the intra-subject information can be taken in from the receiving apparatus 2 via the communication cable 5, and can be displayed on the LCD 41. Therefore, a display unit is not necessary in the receiving apparatus, and a circuit configuration becomes simple. As a result, the receiving apparatus can be made compact and light, and power consumption can be decreased.

In the present embodiment, based on detection of a connection to the receiving apparatus 2, intra-subject information can be displayed on the LCD 41 according to a switch control within the viewer 4 as a compact display device. Therefore, based on a simple operation of connecting the viewer 4 as a compact display device to the receiving apparatus 2, information necessary for the examination such as image data acquired from the capsule endoscope 3 can be promptly displayed in real time in the LCD 41 of the viewer 4 as a compact display device.

Second Embodiment

FIG. 7 is a block diagram showing a configuration of a viewer as a compact display device shown in FIG. 1 according to a second embodiment. Constituent elements similar to those shown in FIG. 4 are denoted with like reference letters or numerals, for the sake of convenience of explanation.

In the present embodiment, the viewer 4 as a compact display device can switch between a radio function that the viewer 4 originally has and a receiving function using a wire explained in the first embodiment. In other words, in the present embodiment, the viewer 4 includes a receiving circuit 58 that receives a radio signal from the receiving antenna 57, and an image processing circuit 59 that image-processes an image signal demodulated by the receiving circuit 58 and outputs the image-processed image data to the changeover switch 44, in addition to the configuration shown in FIG. 4.

When the viewer 4 as a compact display device is in a state before being connected to the receiving apparatus 2 by the communication cable 5, the receiving circuit 58 directly receives an image signal from the capsule endoscope 3. The control unit 49 displays the image data demodulated by the receiving circuit 58 and processed by the image processing circuit 59, on the LCD 41, based on a switch control of the changeover switch 44.

When the communication cable 5 is connected to the receiving apparatus 2 and when the communication-cable connection detector 48 detects the connection, the control unit 49 switch controls the changeover switch 44 to the radio receiving function (at the image processing circuit 43 side), thereby displaying the image data from the receiving apparatus 2 on the LCD 41. In this case, the image data received by the receiving circuit 58 can be stored in an internal memory (not shown), and thereafter, the control unit 49 can control the changeover switch 44 to display the image data on the LCD 41, based on a switch instruction of the operating unit 50. Alternatively, the image data can be abandoned without being displayed in the LCD 41. The operating unit 50 can instruct a display of image data by radio, a display of image data by wire, and a display of position information.

As explained above, in the present embodiment, the control unit 49 switch controls the changeover switch 44 to switch between the display of the image data taken in by wire and the display of image data taken in by radio, based on a connection detection by the communication-cable connection detector 48. Information necessary for the examination such as the intra-subject information can be taken in from the receiving apparatus 2 via the communication cable 5, and displayed in the LCD 41. Therefore, as in the first embodiment, a display unit is not necessary in the receiving apparatus, and the circuit configuration becomes simple. With this arrangement, the receiving apparatus can be made compact and light, and power consumption can be decreased.

Further, in the present embodiment, as in the first embodiment, by detecting a connection between the viewer 4 as a compact display device and the receiving apparatus 2, the radio function that the viewer 4 as a compact display device originally has and the receiving function by wire are switch controlled so that information necessary for the examination can be taken in from the receiving apparatus 2 and displayed in the LCD 41. Therefore, information that is necessary for the examination such as the image data acquired from the capsule endoscope can be promptly displayed in real time on the LCD 41 of the viewer 4 as a compact display device.

INDUSTRIAL APPLICABILITY

As described above, the intra-subject information acquiring system according to the present invention is useful for a medical observation apparatus that is inserted into the inside of a human body and observes a examined part of a subject. Particularly, the intra-subject information acquiring system according to the present invention is useful for decreasing the size and weight of a receiving apparatus and decreasing power consumption.

The invention claimed is:

1. An intra-subject information acquiring system comprising:
    a receiving apparatus that receives intra-subject information radio transmitted from a body-insertable apparatus inserted into a subject;
    a viewer that takes in and displays the intra-subject information on a display unit; and
    a communication unit that connects the receiving apparatus and the viewer in a communicable manner,
  wherein
    the receiving apparatus outputs at least the intra-subject information to the viewer via the communication unit, and
    the viewer includes
      the display unit, a power switch, and an instructing unit that are provided on an external surface thereof,
      a detector that detects a connection between the viewer and the receiving apparatus by the communication unit, and
      a switching controller that switches a display of the display unit to a display of the intra-subject information taken in via the communication unit, based on a result of detection by the detector or a display switch instruction by the instructing unit.

2. The intra-subject information acquiring system according to claim 1, wherein
    the intra-subject information that the body-insertable apparatus transmits includes at least an image signal acquired by imaging of an interior of the subject,
    the receiving apparatus further includes
      a receiving antenna that receives intra-subject information from the body-insertable apparatus,
      a received strength detector that detects received strength in the receiving antenna, and
      a superimposing unit that superimposes information of received strength detected by the received strength detector, onto the intra-subject information, and the viewer further includes
an analyzer that analyzes a position of the body-insertable apparatus, based on information of the received strength.

3. The intra-subject information acquiring system according to claim 1, wherein
the intra-subject information that the body-insertable apparatus transmits includes at least an image signal acquired by imaging an interior of the subject, and position information of the body-insertable apparatus.

4. The intra-subject information acquiring system according to claim 2, wherein
the information displayed on the display unit includes the image signal, information concerning the body-insertable apparatus, information concerning the receiving apparatus, position information of the body-insertable apparatus, information concerning an examination of the subject, and identification information of the subject, and
the display unit displays at least one piece of information among these pieces of information, according to a display switching by the switching controller.

5. The intra-subject information acquiring system according to claim 4, wherein the identification information of the subject includes at least one of a patient ID identifying the subject, a patient name, and an age.

6. The intra-subject information acquiring system according to claim 4, wherein the information concerning the examination of the subject includes at least one of an examination ID of the subject and a time of examination.

7. The intra-subject information acquiring system according to claim 4, wherein the information concerning the body-insertable apparatus includes at least one of a capsule ID identifying the body-insertable apparatus, and a remaining battery charge of the body-insertable apparatus.

8. The intra-subject information acquiring system according to claim 4, wherein the information concerning the receiving apparatus includes at least one of a receiving apparatus ID identifying the receiving apparatus, a remaining battery charge of the receiving apparatus, a receiving state of a radio signal from the body-insertable apparatus, and an alarm issued by the receiving apparatus.

9. The intra-subject information acquiring system according to claim 4, wherein
the communication unit is a communication cable including a USB cable or a 232C cable, and
the receiving apparatus transmits information to be displayed on the display unit via the communication cable to the viewer.

10. The intra-subject information acquiring system according to claim 4, wherein the receiving apparatus superimposes information to be displayed on the display unit onto the image signal, and transmits a resulting superimposed image signal to the viewer via the communication unit.

11. The intra-subject information acquiring system according to claim 3, wherein
the information displayed on the display unit includes the image signal, information concerning the body-insertable apparatus, information concerning the receiving apparatus, position information of the body-insertable apparatus, information concerning an examination of the subject, and identification information of the subject, and
the display unit displays at least one piece of information among these pieces of information, according to a display switching by the switching controller.

12. The intra-subject information acquiring system according to claim 11, wherein the identification information of the subject includes at least one of a patient ID identifying the subject, a patient name, and an age.

13. The intra-subject information acquiring system according to claim 11, wherein the information concerning the examination of the subject includes at least one of an examination ID of the subject and a time of examination.

14. The intra-subject information acquiring system according to claim 11, wherein the information concerning the body-insertable apparatus includes at least one of a capsule ID identifying the body-insertable apparatus, and a remaining battery charge of the body-insertable apparatus.

15. The intra-subject information acquiring system according to claim 11, wherein the information concerning the receiving apparatus includes at least one of a receiving apparatus ID identifying the receiving apparatus, a remaining battery charge of the receiving apparatus, a receiving state of a radio signal from the body-insertable apparatus, and an alarm issued by the receiving apparatus.

16. The intra-subject information acquiring system according to claim 11, wherein
the communication unit is a communication cable including a USB cable or a 232C cable, and
the receiving apparatus transmits information to be displayed on the display unit via the communication cable to the viewer.

17. The intra-subject information acquiring system according to claim 11, wherein the receiving apparatus superimposes information to be displayed on the display unit onto the image signal, and transmits a resulting superimposed image signal to the viewer via the communication unit.

18. An intra-subject information acquiring system comprising:
a receiving apparatus that receives intra-subject information radio transmitted from a body-insertable apparatus inserted into a subject;
a display device that takes in and displays the intra-subject information on a display unit; and
a communication unit that connects the receiving apparatus and the display device in a communicable manner, wherein
the receiving apparatus outputs at least the intra-subject information to the display device via the communication unit, and
the display device includes
a detector that detects a connection between the display device and the receiving apparatus by the communication unit,
a radio unit that receives intra-subject information radio transmitted from the body-insertable apparatus, and
a switching controller that switch controls a reception operation performed by the radio unit or the communication unit, based on a result of detection by the detector.

19. The intra-subject information acquiring system according to claim 18, wherein
the intra-subject information that the body-insertable apparatus transmits includes at least an image signal acquired by imaging of an interior of the subject,
the receiving apparatus further includes
a receiving antenna that receives intra-subject information from the body-insertable apparatus,
a received strength detector that detects received strength in the receiving antenna, and a superimposing unit that superimposes information of received strength detected by the received strength detector, onto the intra-subject information, and the display apparatus further includes
an analyzer that analyzes a position of the body-insertable apparatus, based on information of the received strength, and
an instructing unit that instructs information displayed on the display unit, and the switching controller switches information displayed on the display unit, according to an instruction of the instructing unit.

20. The intra-subject information acquiring system according to claim 19, wherein the information displayed on the display unit includes the image signal, information concerning the body-insertable apparatus, information concerning the receiving apparatus, position information of the body-insertable apparatus, information concerning an examination of the subject, and identification information of the subject, and the display unit displays at least one piece of information among these pieces of information, according to a display switching by the switching controller.

21. The intra-subject information acquiring system according to claim 20, wherein the identification information of the subject includes at least one of a patient ID identifying the subject, a patient name, and an age.

22. The intra-subject information acquiring system according to claim 20, wherein the information concerning the examination of the subject includes at least one of an examination ID of the subject and a time of examination.

23. The intra-subject information acquiring system according to claim 20, wherein the information concerning the body-insertable apparatus includes at least one of a capsule ID identifying the body-insertable apparatus, and a remaining battery charge of the body-insertable apparatus.

24. The intra-subject information acquiring system according to claim 20, wherein the information concerning the receiving apparatus includes at least one of a receiving apparatus ID identifying the receiving apparatus, a remaining battery charge of the receiving apparatus, a receiving state of a radio signal from the body-insertable apparatus, and an alarm issued by the receiving apparatus.

25. The intra-subject information acquiring system according to claim 20, wherein the communication unit is a communication cable including a USB cable or a 232C cable, and the receiving apparatus transmits information to be displayed on the display unit via the communication cable to the display device.

26. The intra-subject information acquiring system according to claim 20, wherein the receiving apparatus superimposes information to be displayed on the display unit onto the image signal, and transmits a resulting superimposed image signal to the display device via the communication unit.

27. The intra-subject information acquiring system according to claim 20, wherein the display device further includes a changeover switch to selectively switch the information displayed on the display unit among the image signal, the information concerning the body-insertable apparatus, the information concerning the receiving apparatus, the position information of the body-insertable apparatus, the information concerning the examination of the subject, and the identification information of the subject, and the switching controller switch controls the changeover switch.

28. The intra-subject information acquiring system according to claim 18, wherein the intra-subject information that the body-insertable apparatus transmits includes at least an image signal acquired by imaging an interior of the subject, and position information of the body-insertable apparatus, the display device further includes
an instructing unit that instructs information to be displayed on the display unit, and the switching controller switches information displayed on the display unit, according to an instruction of the instructing unit.

29. The intra-subject information acquiring system according to claim 28, wherein the information displayed on the display unit includes the image signal, information concerning the body-insertable apparatus, information concerning the receiving apparatus, position information of the body-insertable apparatus, information concerning an examination of the subject, and identification information of the subject, and the display unit displays at least one piece of information among these pieces of information, according to a display switching by the switching controller.

30. The intra-subject information acquiring system according to claim 29, wherein the identification information of the subject includes at least one of a patient ID identifying the subject, a patient name, and an age.

31. The intra-subject information acquiring system according to claim 29, wherein the information concerning the examination of the subject includes at least one of an examination ID of the subject and a time of examination.

32. The intra-subject information acquiring system according to claim 29, wherein the information concerning the body-insertable apparatus includes at least one of a capsule ID identifying the body-insertable apparatus, and a remaining battery charge of the body-insertable apparatus.

33. The intra-subject information acquiring system according to claim 29, wherein the information concerning the receiving apparatus includes at least one of a receiving apparatus ID identifying the receiving apparatus, a remaining battery charge of the receiving apparatus, a receiving state of a radio signal from the body-insertable apparatus, and an alarm issued by the receiving apparatus.

34. The intra-subject information acquiring system according to claim 29, wherein the communication unit is a communication cable including a USB cable or a 232C cable, and the receiving apparatus transmits information to be displayed on the display unit via the communication cable to the display device.

35. The intra-subject information acquiring system according to claim 29, wherein the receiving apparatus superimposes information to be displayed on the display unit onto the image signal, and transmits a resulting superimposed image signal to the display device via the communication unit.

36. The intra-subject information acquiring system according to claim 29, wherein the display device further includes a changeover switch to selectively switch the information displayed on the display unit among the image signal, the information concerning the body-insertable apparatus, the information concerning the receiving apparatus, the position information of the body-insertable apparatus, the information concerning the examination of the subject, and the identification information of the subject, and the switching controller switch controls the changeover switch.

* * * * *